United States Patent
Toderi et al.

[11] Patent Number: 6,162,914
[45] Date of Patent: Dec. 19, 2000

[54] PROCESS FOR THE REDUCTION OF PTERINS

[75] Inventors: Nando Toderi, Agno; Fabrizio Marazza, Navoggio, both of Switzerland

[73] Assignee: Cerbios-Pharma S.A., Switzerland

[21] Appl. No.: 09/306,996

[22] Filed: May 7, 1999

Related U.S. Application Data

[63] Continuation of application No. 09/065,722, Apr. 24, 1998.

[51] Int. Cl.$^7$ ................................................. C07D 475/04
[52] U.S. Cl. ........................................ 544/258; 544/258
[58] Field of Search ............................................. 544/258

[56] References Cited

U.S. PATENT DOCUMENTS

| | | | |
|---|---|---|---|
| 2,790,802 | 7/1957 | Brockman | 574/258 |
| 2,927,113 | 3/1960 | D'Amato | 544/258 |
| 4,206,307 | 6/1980 | Temple | 544/258 |
| 4,540,783 | 9/1985 | Vissontivi | 544/258 |
| 4,595,752 | 6/1986 | Azuma | 544/258 |
| 4,665,176 | 5/1987 | Hirai | 544/258 |
| 4,665,182 | 5/1987 | Nichol | 544/258 |
| 4,701,455 | 10/1987 | Nichol | 544/258 |
| 4,959,472 | 9/1990 | Wood et al. | 544/258 |
| 5,106,974 | 4/1992 | Akimoto et al. | 544/280 |
| 5,124,452 | 6/1992 | Gennari | 544/258 |
| 5,350,850 | 9/1994 | Vecchi | 544/258 |
| 5,354,734 | 10/1994 | Akimoto et al. | 544/250 |
| 5,354,754 | 10/1994 | Akimoto et al. | 544/250 |
| 5,554,615 | 9/1996 | Nomura et al. | 544/280 |

FOREIGN PATENT DOCUMENTS

| | | |
|---|---|---|
| 608002 | 7/1994 | European Pat. Off. |
| 635 344 | 3/1983 | Switzerland . |
| 635344 | 3/1983 | Switzerland . |

*Primary Examiner*—Mukund J. Shah
*Assistant Examiner*—Ben Schroeder
*Attorney, Agent, or Firm*—Burns, Doane, Swecker & Mathis, L.L.P.

[57] ABSTRACT

The inventive process for the reduction of pterins by means of an alkali metal boron hydride in water to the corresponding 5,6,7,8-tetrahydropterins is characterized in that the reduction is carried out in the presence of a catalytical amount of a water-soluble Pb(II)-salt.

16 Claims, No Drawings

PROCESS FOR THE REDUCTION OF PTERINS

This application is a continuation of application Ser. No. 09/065,722 filed Apr. 24, 1998.

FIELD OF THE INVENTION

The present invention is directed to a process for the reduction of pterins.

BACKGROUND OF THE INVENTION

Folic acid may be reduced to 5,6,7,8-tetrahydrofolic acid (hereinafter abbreviated as THF) either by catalytic hydrogenation or through the use of $NaBH_4$. See, for example, CH PS 635 344 for a summary.

THF is the starting material for the preparation of N(5)-formyl-THF, known as folinic acid or leucovorin, and of N(5)-methyl-THF. These two compounds have a great pharmacological usefulness as vitaminic preparations and as rescue agents in cancer chemotherapy. See, for example, EP 0 409 125.

The reduction of folic acid by catalytic hydrogenation, or through the use of $NaBH_4$, however, produces strongly contaminated THF, which, due to its inherent instability, may not be purified.

The conventional reduction of folic acid with $NaBH_4$ also requires a considerable excess of $NaBH_4$ (5 to 30 mole per mole folic acid). This reduction runs only at elevated temperatures (60° C. to 80° C.).

Unpurified THF may be further processed to N(5)-formyl-THF or N(5)-methyl-THF through the use of complicated processes. See CH PS 635 344.

An improved $NaBH_4$ reduction of folic acid is described in TC. Temple et al., J. Med. Chem. (1979), 22, 731. This reduction runs at room temperature, but still requires a considerable excess of $NaBH_4$ (about 10 mole per mole folic acid). Due to this considerable excess of $NaBH_4$, the industrial scale reduction of folic acid by this method does not make sense. Safety concerns due to the danger of explosion also make this method less attractive.

EP 0 608 002 further discloses the reduction of 1 mole folic acid with about 10 mole $NaBH_4$.

Metal catalyzed $NaBH_4$ reductions of various substrates, such as ketones, esters, acyl halides, aromatic systems, etc., are known. See *Sodium Borchydride Digest*, (1995), 3rd ed., Morton International Inc. Catalysts such as Cu(II), Ni(II), Co(II), and lanthanide-salts are used in these $NaBH_4$ reductions.

OBJECTS OF THE INVENTION

It is an object of the present invention to provide a process for the reduction of pterins with an alkali metal boron hydride in which the respective reduction product is obtained without considerable contaminations.

In this process shall be used only a small excess of reducing agent.

This process shall run at low temperature, especially in the range from 0° C. to 25° C.

This process shall be realizable with little expenditure in industrial scale.

Quite surprisingly it has been found that the above mentioned objects are reached, when the reduction is carried out in the presence of a catalytical amount of a water-soluble Pb(II)-salt.

SUMMARY OF THE INVENTION

The inventive process for the reduction of pterins of the general formula I

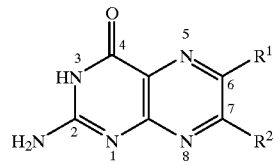

wherein
$R^1$ is hydrogen, a $C_1$ to $C_3$-alkyl group, a 1,2-dihydroxypropyl group, a residue of the formula II

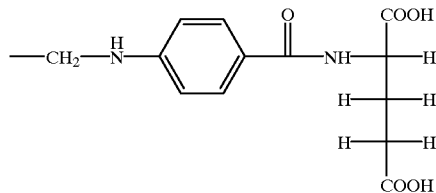

or
a residue of the formula III

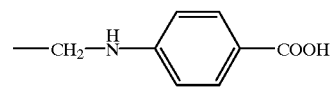

and,
$R^2$ is hydrogen, a $C_1$ to $C_3$-alkyl group or a 1,2-dihydroxypropyl group,
whereby, when $R^2$ is a 1,2-dihydroxypropyl group, $R^1$ must be hydrogen or a $C_1$ to $C_3$-alkyl group,
by means of an alkali metal boron hydride in water to 5,6,7,8-tetrahydropterins of the general formula IV

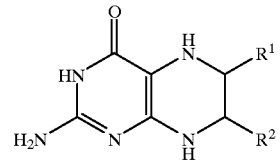

wherein
$R^1$ and $R^2$ have the above given definitions,
is characterized in that the reduction is carried out in the presence of a catalytical amount of a water-soluble Pb(II)-salt.

DESCRIPTION OF THE PREFERRED EMBODIMENTS

The inventive process for the reduction of pterins of the general formula I by means of an alkali metal boron hydride is preferably performed using sodium borohydride as the alkali metal boron hydride. Folic acid is a preferred compound of formula I. The reduction may be carried out in the presence of a buffer and/or antioxidizing agent; citric acid may be used as the buffer and/or antioxidizing agent, for example.

Reduction reaction conditions of pH-value in the range from 7.5 to 10.0, especially 8.3 to 8.8 may be used. The addition of the alkali metal boron hydride, especially sodium borohydride, is preferably carried out at a temperature in the range of 0° C. to 10° C., especially 5° C. to 10° C., and the completion of the reduction is preferably carried out at a temperature of from 15° C. to 25° C.

The reduction reaction may be further characterized in terms of the ratios of the components present. For example, the molar ratio of the alkali metal boron hydride to the pterin of formula I to be reduced may be from 1.0 to 3.2, preferably 2.0. In addition, the molar ratio of the Pb(II)-salt to alkali metal boron hydride may be from $10^{-5}$ to $10^{-3}$, preferably $10^{-5}$.

The Pb(II)-salt is preferably lead chloride, lead acetate or lead nitrate.

The mechanism of the inventive Pb (II)-catalyzed reaction is not known at the moment of the filing of this invention.

With usual transition metal salts, as for example Fe(II), Co(II), Ni(II), Cu(II), Zn(II), the inventive process may not be carried out.

In general, the tetrahydropterins prepared with the inventive, process have a chromatgraphical purity of more than 95%.

It is preferred to prepare THF from folic acid with the inventive process.

The so prepared THF has a chromatographical purity of more than 96% and thus is suitable for the synthesis of N(5)-formyl-THF or N(5)-methyl-THF having pharmacological qualities; see NO 172 492.

The following examples shall illustrate the present invention.

EXAMPLE 1

16.75 g (41 mmole) of folic acid with a water content of about 8% were suspended in a solution of 17.5 mg (0.053 mmoles) $Pb(NO_3)_2$ in 200 ml deionized water.

The pH of the mixture was adjusted to 7.5 by the dropwise addition of 20% NaOH under vigorous stirring at room temperature.

A clear solution which was obtained was cooled to a temperature of 10° C.

A solution of 5.0 g (132 mmoles) $NaBH_4$ in 25 ml deionized water was added dropwise over 20 minutes and under stirring at this temperature. The temperature was kept at 10° C. during this addition.

During this addition the pH-value of the mixture was kept between 8.5 and 8.8 by means of the dropwise addition of 20% aqueous citric acid.

After the finished $NaBH_4$-addition the temperature was allowed to increase to 23° C. under stirring, and it was stirred at this temperature for 2 further hours.

Then this solution was cooled to a temperature of 10° C. and under vigorous stirring was added dropwise 18% HCl during such a long time until the mixture had a pH-value of 3.6.

During this acidification the THF precipitated.

The precipitated THF was isolated by means of filtration, washed once with degased and deionized water and once with 90% ethanol.

The so obtained solid was dried under reduced pressure.

There were obtained 15.7 g THF.

A HPLC-analysis of this product showed a purity of 96.3%.

EXAMPLE 2

16.75 g (41 mmole) of folic acid were reduced as described in example 1 but without the addition of $Pb(NO_3)_2$.

The HPLC-analysis of the isolated product showed a purity of 49.0%.

What is claimed is:

1. A process for the reduction of pterins of the formula I

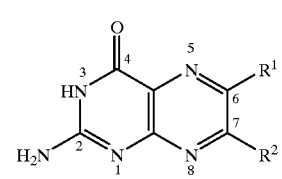

(I)

wherein $R^1$ is hydrogen, a $C_1$ to $C_3$-alkyl group, a 1,2-dihydroxypropyl group), a residue of the formula II

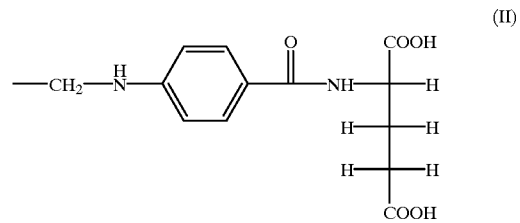

(II)

or a residue of the formula III

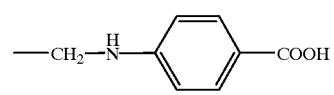

(III)

and, $R^2$ is hydrogen, a $C_1$ to $C_3$-alkyl group or a 1,2-dihydroxypropyl group, whereby, when $R^2$ is a 1,2-dihydroxypropyl group, $R^1$ must be hydrogen or a $C_1$ to $C_3$-alkyl group, by means of an alkali metal boron hydride in water to 5,6,7,8-tetrahydropterins of the general formula IV

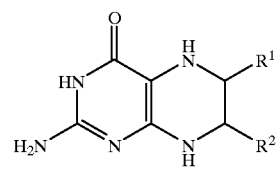

(IV)

wherein

R$^1$ and R$^2$ have the above given definitions, characterized in that the reduction is carried out in the presence of a catalytical amount of a water-soluble Pb(II)-salt.

2. The process according to claim 1, characterized in that the reduction is carried out in the presence of a buffer.

3. The process according to claim 1, characterized in that the reduction is carried out in the presence of an antioxidizing agent.

4. The process according to claim 1, characterized in that the reduction is carried out at a pH-value in the range from 7.5 to 10.0.

5. The process according to claim 1, characterized in that the addition of the alkali metal boron hydride, is carried out at a temperature in the range from 0° C. to 10° C., and that the completion of the reduction is carried out at a temperature from 15° C. to 25° C.

6. The process according to claim 1, characterized in that the molar ratio from alkali metal boron hydride to the pterin of the formula I to be reduced is from 1.0 to 3.2.

7. The process according to claim 1, characterized in that the molar ratio from Pb(II)-salt to alkali metal boron hydride is from $10^{-5}$ to $10^{-3}$.

8. The process according to claim 1, characterized in that the Pb(II)-salt is lead chloride, lead acetate or lead nitrate.

9. The process according to claim 1, characterized in that the compound of the formula I is folic acid.

10. The process according to claim 2, wherein the buffer is citric acid.

11. The process according to claim 3, wherein the antioxidizing agent is citric acid.

12. The process according to claim 4, wherein the reduction is carried out at a pH-value in the range from 8.3 to 8.8.

13. The process according to claim 5, wherein the alkali metal boron hydride is sodium borohydride.

14. The process according to claim 5 wherein the addition of the alkali metal boron hydride is carried out at a temperature in the range from 5° C. to 10° C.

15. A The process according to claim 6, wherein the molar ratio from alkali metal boron hydride to the pterin of the formula I to be reduced is 2.0.

16. The process according to claim 7, wherein the molar ratio from Pb(II)-salt to alkali metal boron hydride is $10^{-5}$.

* * * * *

UNITED STATES PATENT AND TRADEMARK OFFICE
CERTIFICATE OF CORRECTION

PATENT NO. : 6,162,914
DATED : December 19, 2000
INVENTOR(S) : Nando Toderi and Fabrizio Marazza It is certified that error appears in the above-identified patent and that said Letters Patent is hereby corrected as shown below:

<u>Title page,</u>
Insert the following:

-- [30]   Foreign Application Priority Data
   Apr. 26, 1997   [CH]   Switzerland ................... 1997-0967-97 --

Signed and Sealed this

Fourteenth Day of May, 2002

Attest:

Attesting Officer

JAMES E. ROGAN
Director of the United States Patent and Trademark Office